(12) United States Patent
Stuart et al.

(10) Patent No.: US 7,790,442 B2
(45) Date of Patent: Sep. 7, 2010

(54) BACTERIORHODOPSIN-BASED PHOTOCHROMIC SENSOR FOR DETECTION OF CHEMICAL AND ENVIRONMENTAL TOXINS

(75) Inventors: Jeffrey A. Stuart, Columbia, CT (US); Duane Marcy, Syracuse, NY (US); Robert R. Birge, Coventry, CT (US)

(73) Assignee: Syracuse University, Syracuse, NY (US)

( * ) Notice: Subject to any disclaimer, the term of this patent is extended or adjusted under 35 U.S.C. 154(b) by 304 days.

(21) Appl. No.: 11/779,963

(22) Filed: Jul. 19, 2007

(65) Prior Publication Data

US 2008/0057490 A1    Mar. 6, 2008

Related U.S. Application Data

(60) Provisional application No. 60/807,729, filed on Jul. 19, 2006.

(51) Int. Cl.
*C12M 3/00* (2006.01)

(52) U.S. Cl. .............. 435/288.7; 422/82.05; 422/82.08; 435/808; 436/164; 436/172; 436/805

(58) Field of Classification Search ........................ None
See application file for complete search history.

(56) References Cited

U.S. PATENT DOCUMENTS 7,103,242 B2 * 9/2006 Gopalkrishna ............... 385/16
2002/0127623 A1 * 9/2002 Minshull et al. ........... 435/7.92

\* cited by examiner

*Primary Examiner*—Christopher L Chin
(74) *Attorney, Agent, or Firm*—George R. McGuire; David L. Nocilly; Bond Schoeneck & King, PLLC

(57) ABSTRACT

A bacteriorhodopsin based chemical sensing architecture based upon the collective response of bacteriorhodopsin and a number of its mutants; the wild type protein and a selection of genetically-engineered variants was able to respond differentially to a selection of amines. The observable response to the presence of a target chemical was manifested through a modulation of bacteriorhodopsin's photokinetic properties, which are monitored through pump-probe techniques using a custom prototype flash photolysis system. Differential responsivity exists at two levels; (1) bacteriorhodopsin proteins (wild-type and genetically-engineered variants) respond differentially upon exposure of a target chemical, and (2) the response pattern exhibited by the proteins differs from chemical to chemical. This dichotomy forms the basis for a BR-mediated chemical sensing technology that is highly sensitive and selective and may therefore discriminate between different chemicals.

7 Claims, 8 Drawing Sheets

The Bacteriorhodopsin Mutant Matrix Sensor: BR mutant protein-based sensor elements are activated by light, and the resulting photocycle kinetics for the M- and O-states can be used to identify the chemical interacting with the sensor.

BACTERIORHODOPSIN-BASED PHOTOCHROMIC SENSOR FOR DETECTION OF CHEMICAL AND ENVIRONMENTAL TOXINS

CROSS-REFERENCE TO RELATED APPLICATION

The present application claims priority to U.S. Provisional Application No. 60/807,729, filed on Jul. 19, 2006.

BACKGROUND OF THE INVENTION

1. Field of the Invention

The present invention relates to chemical sensing architectures and, more specifically, to a bacteriorhodopsin based chemical sensor.

2. Description of the Related Art

The motivating force behind sensor technology of any type is health. Whether it be defined in terms of human, machine, building, system, or the environment, health maintenance is critical in today's society. The factor to be sensed depends on the application; mechanical stress, pressure, temperature, light flux, and chemical or biological contamination are all common targets of sensor architectures. Perhaps the largest motivation in sensor technology development is found within the last two examples, the ability to detect compounds, toxins, or organisms deleterious to human health. A number of different sensor architectures are currently being explored, but the most prominent are efforts to mimic biological detection schemes. In an effort to model the mechanisms for biological chemical detection (i.e., smell and taste), researchers are moving away from specific detection interactions (favoring detection of a single chemical species or class of molecules), toward architectures that examine the collective responses of larger numbers of sensors that are characterized by non-specific molecular interactions. These technologies are typically referred to as electronic noses.

One approach to sensor design that has been explored very little to date, at least from the perspective of electronic nose technology, is that of hybrid architectures employing biological molecules as an active element of the detection scheme. There are several conceivable reasons as to why this approach has not been widely explored, such as stability and state determination. Complex biological molecules are not generally known for their inherent stability, and the ability to interrogate for the purpose of state determination requires some sort of signal transduction mechanism. Although many proteins act as signal transducers, few perform that function outside the confines of a biological organism and the transduction mechanisms that are employed inside the organism are not easily adapted to non-biological environments, at least not in a way that the signal of interest can be amplified and detected. One protein, Bacteriorhodopsin, or BR, does not suffer from these disadvantages, but has never been successfully adapted for use in a commercially viable sensor.

SUMMARY OF THE INVENTION

It is therefore a principal object and advantage of the present invention to provide a sensor for detecting the presence of chemicals using bacteriorhodopsin.

It is another object and advantage of the present invention to provide a sensor for detecting chemicals that is highly selective.

It is an additional object and advantage of the present invention to provide a sensor for detecting chemicals that is highly sensitive.

In accordance with the foregoing objects and advantages, the present invention provides a sensor for detecting chemicals comprising the detection of changes in the optical response of bacteriorhodopsin in the presence of a target chemical or compound. The sensor generally comprises a monochromatic light source for initiating the photo-cycle, a sample cube containing bacteriorhodopsin and a target chemical, a first lens for directing light from the source onto the cube, a detector for identifying the frequency of light passing through the sample cube, and a second lens for directing light passing through the sample cube onto the detector. The presence of, and changes in the concentration of various chemicals, may be detected by measuring the effect of the optical response on various mutants of bacteriorhodopsin.

BRIEF DESCRIPTION OF THE DRAWINGS

The present invention will be more fully understood and appreciated by reading the following Detailed Description in conjunction with the accompanying drawings, in which.

DETAILED DESCRIPTION

Bacteriorhodopsin, or BR, occurs as an integral membrane protein in *Halobacterium salinarum*, an archaebacterium common in salt marshes where the concentration of sodium chloride is >4M. It is typically isolated from the native organism as patches of purple membrane, consisting of roughly 75% BR & 25% lipid. Its role in nature is to serve as a light to chemical energy transducer by creating a light-induced proton gradient across the cell membrane. This pH gradient is harnessed by the cell to do work. The chromophore responsible for absorption of light by the protein is all-trans retinal, a derivative of Vitamin A, which is bound via a protonated Schiff base to Lys-216. Light induces an all-trans to 13-cis isomerization in the chromophore, followed by a series of thermal protein intermediates characterized by different absorption spectra, vectoral proton transport, and ultimately the reisomerization of the chromophore with consequent regeneration of the bR resting state.

Figure 1:
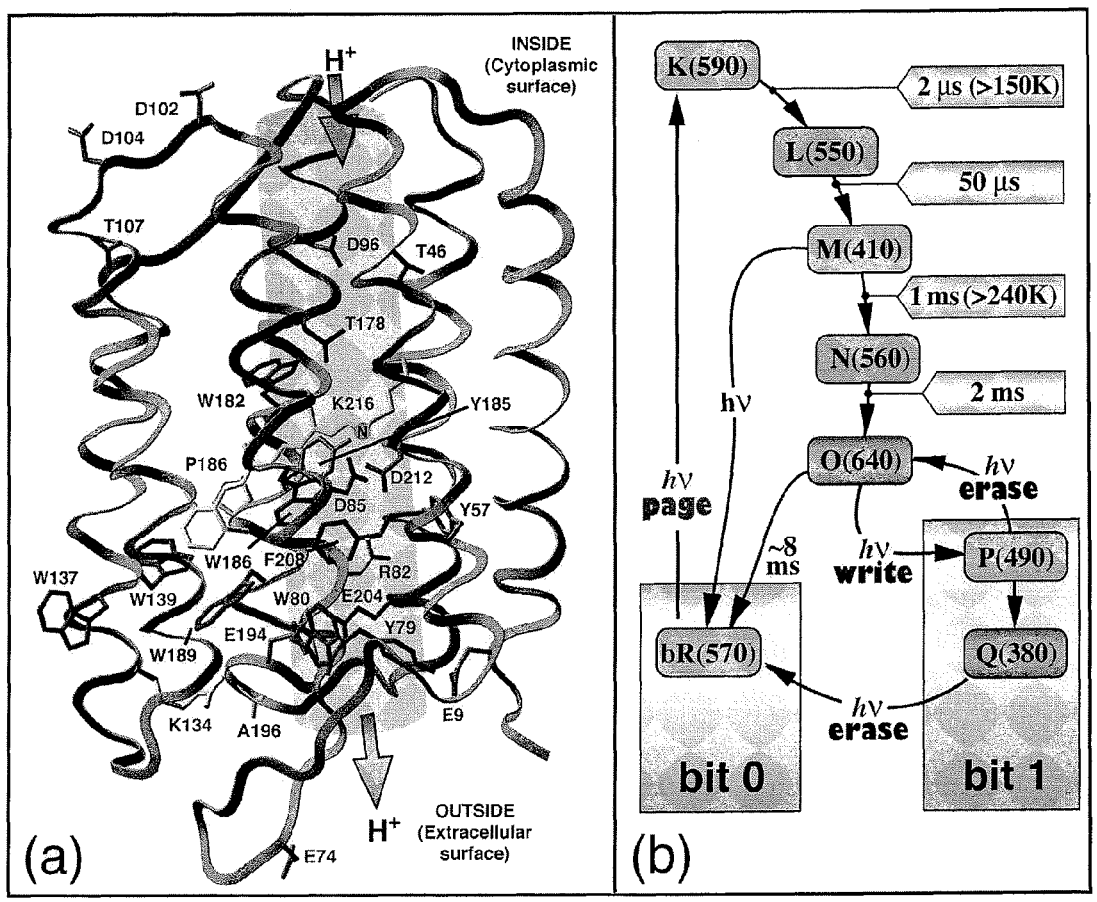
FIG. 1(a) is a schematic of protein structure, illustrating the chromophore, the protein backbone, and key amino acids involved in function.
FIG. 1(b) is a schematic of the BR Photocycle, illustrating the main intermediate states, along with $\lambda$max and the branched photocycle.

FIG. 1 illustrates the basic photocycle of bacteriorhodopsin upon the absorption of light, the all-trans retinal chromophore embedded within the protein isomerizes to 13-cis, resulting in the formation of the K-state, the only photochemically generated state in the photocycle. The remainder of the intermediates are thermal, being driven by the chemical energy stored in the protein as a result of the initial photon absorption. During the remainder of the photocycle, L through O, the chromophore is reisomerized and a proton is translocated across the membrane, thereby resetting the bR resting state, and priming the protein for absorption of the next photon. At room temperature, the photocycle is completed in roughly 10 ms. Several of the intermediates are known to be photochemically active, including the M and O states. Upon absorption of blue light, the M state is driven back to the bR resting state. The O-state is the gateway to the branched photocycle, consisting of the P & Q states. These intermediates have applications in three-dimensional optical memory storage, and are the first truly permanent intermediates described in the photocycle. A parallel research effort funded by NYS Infotonics is evaluating the potential of the branched photocycle for volumetric holographic and associative memory applications. Aside from the branched photocycle, the bR, M, and O states are the most important with respect to applications in biomolecular electronics, for three primary reasons: they are the most easily detected intermediates in the photocycle, they are extremely sensitive to the chemical environment experienced by the protein, and they are the most spectrally distinct intermediates in the photocycle. Furthermore, the M & O states are longest lived of the intermediates, allowing them to accumulate into easily detectable quantities in the native photocycle. And finally, both of these states have been the target of numerous molecular biology studies, which have produced a large number of genetically engineered variants. These mutant proteins have yielded a wealth of understanding of both the M & O states, making them the best characterized of the BR photocycle. Many of the genetic analogs are easily produced and have already been evaluated for device applications.

Figure 2:
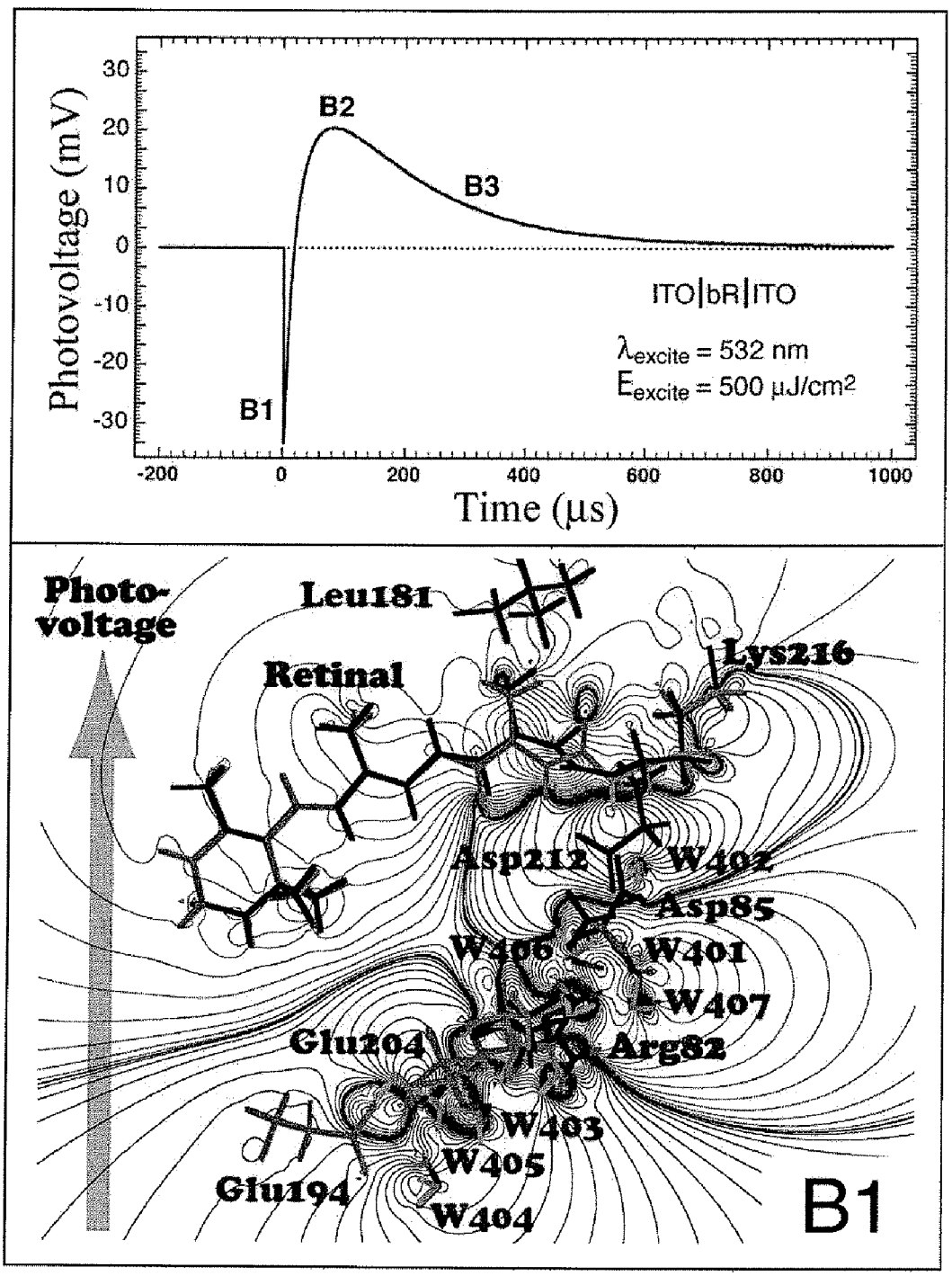
FIG. 2(a) is a diagram of the bacteriorhodopsin photoelectric effect showing three components.
FIG. 2(b) is a diagram of the bacteriorhodopsin photoelectric effect showing the movement of a specific amino acid in response to chromophore isomerization.

In addition to the BR's optical response to light, the protein also exhibits a well defined photoelectric or photovoltaic response upon absorption of a photon. The origins of the signal involve both the movement of the positively charged Schiff base upon isomerization of the chromophore, as well as a concomitant shift of charge along the retinal polyene chain, towards the Schiff base. FIG. 2 illustrates the effect, which can be classified based on time scale. The B1 signal has a rise time of less than 5 ps and is associated with the formation of the K state. The B1 component is likely attributable to partial chromophore isomerization and a coupled motion of Arg-82 toward the primary counterions, Asps 85 and 212. Attempts to correlate B2 and B3 with photocycle intermediates is difficult and a source of some disagreement in the literature. A secondary photoelectric effect on a millisecond time scale is associated with proton translocation in the channel (a light-induced photocurrent). Both of these responses to light have the potential to be exploited for device applications, including sensors, artificial retinas, and as photosensitive microelectronic devices (e.g., use of the protein as the gate in a traditional MOS field effect transistor).

BR possesses a number of appealing characteristics: (1) the protein is inherently rugged and robust, and is resistant to both thermal and photochemical damage (a result of evolving in a harsh environment); (2) high cyclicity (the average number of times the protein can photocycle prior to degradation) on the order of 106 or better, considerably higher than most synthetic photochromic materials; (3) the protein is inherently radiation hardened and protected from free radical degradation; and (4) the primary photochemical event, i.e., absorption of a photon and consequent formation of the K state as a result of retinal isomerization, proceeds with a very high quantum efficiency of roughly 65%. This means that for every 100 photons absorbed by the protein, 65 will result in a photochemical transition. In addition, the semi-crystalline arrangement of the protein as an array of trimers in the membrane also imparts tremendous stability.

Figure 3:
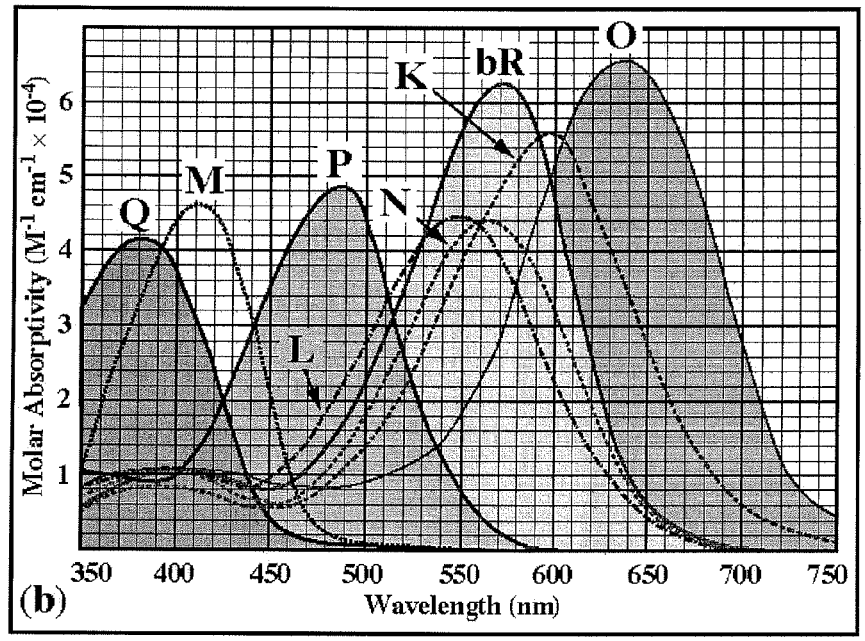
FIG. 3 is a graph of the simulated absorption spectra of the intermediaries in the BR photocycle.
Figure 4:
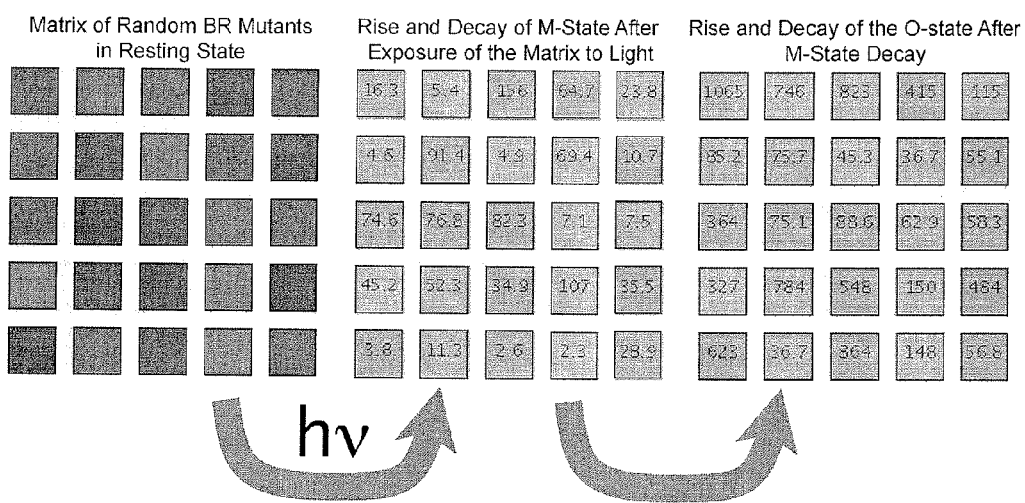
FIG. 4 is a diagram of a bacteriorhodopsin mutant matrix sensor according to the present invention.

FIG. 3 illustrates the absorption spectra of the various BR intermediates, several of which are important to the application of the protein as an active element in biomolecular electronics. Among the earliest applications of bacteriorhodopsin were holographic films, utilizing the bR and the M intermediates, as mentioned above. Early attempts to utilize this binary pair depended upon the ability to extend the M-state lifetime through chemical means; the M-state is sensitive to any environment or chemical that decreases proton mobility, including high pH, quaternary amines, glycerin, etc. This represented the first attempt to exploit bacteriorhodopsin's sensitivity to its chemical environment for device applications. Since then a number of bacteriorhodopsin analogs have been developed that exhibit modulated responses to environmental stimuli, through chemical additives to the protein environment, chemical modification of the retinal chromophore, and genetic manipulation of the protein itself. Perhaps the most versatile aspect of bacteriorhodopsin's utility as a photoactive element device applications is the ability to interrogate the protein by multiple means, by examining modulation of either the optical or photovoltaic properties as a result of external stimuli.

The high quantum efficiency, large oscillator strength, broad-band absorptivity, thermal stability, and fast photovoltaic response of the protein make it an attractive material as the photoactive element in high-speed photodetectors. Such applications include high speed tracking, motion and edge detection as well as high resolution imaging. The significant potential of BR as a light-transducing material was recently shown in a hybrid protein-semiconductor monolithically integrated transimpedance photoreceiver. In this device, the photovoltage generated by the protein biases the gate of an amplifying field effect transistor (FET), creating a photocurrent signal that is further amplified as a current or voltage signal in subsequent transistor-based amplifying stages. The optoelectronic integrated circuit (OEIC), uses the protein as a photodetector, demonstrating performance characteristics comparable to, or better than all-semiconductor OEIC photoreceivers.

BR is an extremely sensitive register of its environment, and has been long known to display an extreme sensitivity to environmental conditions such as pH, relative humidity and ionic strength. The effects of this sensitivity are manifested through modulations in the photocycle and/or the photovoltaic signal. Furthermore, various chemicals have well-defined effects on the protein. Among the classes of chemicals that modulate bacteriorhodopsin's photokinetic behavior include alcohols (methanol, ethanol, propanol, and butanol) and anesthetics. Azides are also known to modulate BR's photophysical properties. Sensitivity of the protein to alcohols is manifested in the form of modulations of the light-induced photocurrent of the protein (i.e., the proton pump efficiency), and could be enhanced by chemical modification of the chromophore or genetic manipulation of the protein. Generally speaking, chemical agents have several modes by which they can modulate protein response, including direct interaction with, or binding to, the protein, and/or indirect interaction by absorption into the lipids proximal to the protein.

The basis for a chemical sensor technology employing bacteriorhodopsin is founded in the protein's sensitivity to its chemical environment. A sensor platform based upon one active sensing element would be extremely limited, and exceedingly impractical. However, bacteriorhodopsin has a distinct advantage over many conventional materials, in that it can be modified through several approaches. The most powerful approach is genetic engineering, whereby the protein can be manipulated at the genetic level, resulting in variants that will exhibit a range of distinct properties. There are methods by which proteins can be modified toward specific goals; for example, increased sensitivity to a specific compound or class of compounds might be introduced through the genetic-engineering techniques of random mutagenesis and directed evolution. However, given that superior sensor architectures are being developed through nonspecific sensing elements, production of highly selective BR variants would defeat the purpose of an electronic nose.

The present invention is based on the capability of wild type bacteriorhodopsin to respond to changes in its chemical environment. Genetically engineered variants would be expected to also exhibit differential sensitivity, whereby each would respond differently to a given target chemical. Monitoring a group of such BR variant proteins results in a numeric matrix, or fingerprint, for each target chemical exposed to the sensor. Denoted as the "Mutant Matrix," this collection of BR variants forms the basis for a protein-based electronic "nose." It should also be recognized by those of skill in the art that proteins such as proteorhodopsin would behave in like fashion and thus may be implemented in the present invention.

At least three numeric fingerprints are possible for each chemical detected, based upon interrogating the BR-based sensor elements for photocycle kinetics (of both M and O states) and the photoelectric effect; the combination of an adequate matrix size with multiple modes of interrogation should help reduce false positive detection events.

The basic element of the present invention is a sensor platform that can quickly and easily measure the protein's response upon exposure to a target chemical. A chemical sensor must function by observing the photocycle of bacteriorhodopsin (BR) and its mutants. The method that is most commonly used to observe the photocycle is a pump-probe experiment known as flash photolysis. A dim continuous light (probe) passes through the sample. The light is too dim to excite the photocycle in the bR. The probe light can be either white light to generate a spectral response, or a monochromatic light to generate a kinetic response. Commercial instrumentation exists to perform this operation (such as that available from OLIS or Edinburgh Instruments). As this instrumentation is large and expensive, it not suitable to chemical sensor application. Accordingly, the present invention encompasses a new flash photolysis system and method.

The key item that must be eliminated from the commercially available instruments is the pulsed gas laser that is used as the pump beam source as such lasers have delicate optics, are large and heavy, are typically water cooled, and are extremely expensive. An alternative is a semiconductor diode laser, which is lightweight, rugged, and is relatively less expensive. The pulse energy derived from a gas laser is on the order of 10-100 mJ, while the diode laser can only produce a pulse on the order of 1-10 µJ. The difference is a factor of 10,000 with a corresponding decrease in signal size of the some amount. As a result, the present invention requires a much more sensitive detector.

Figure 5:
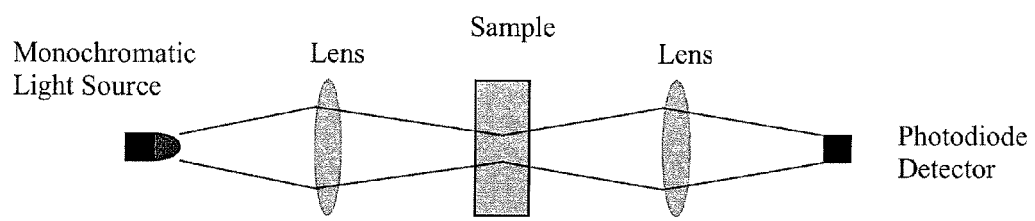
FIG. 5 is a schematic of the optical light path of a probe beam according to the present invention.

In current commercial instruments, either a CCD camera or a photo-multiplier tube is used as the detector. For the purposes of a chemical sensor platform, neither of these systems can be used because of size and cost. A sensor based on the photodiode must be developed for the present invention. Finally, the probe light source, which is most commonly a high-power tungsten-halogen lamp, must be replaced with an LED. The present invention thus constitutes a functioning flash photolysis system that uses an LED as the probe light source and a semiconductor diode laser as a pump light source. In addition, absorbance changes are detected using a photodiode amplifier circuit. A diagram of the probe beam light path is depicted in FIG. 5.

Figure 6:
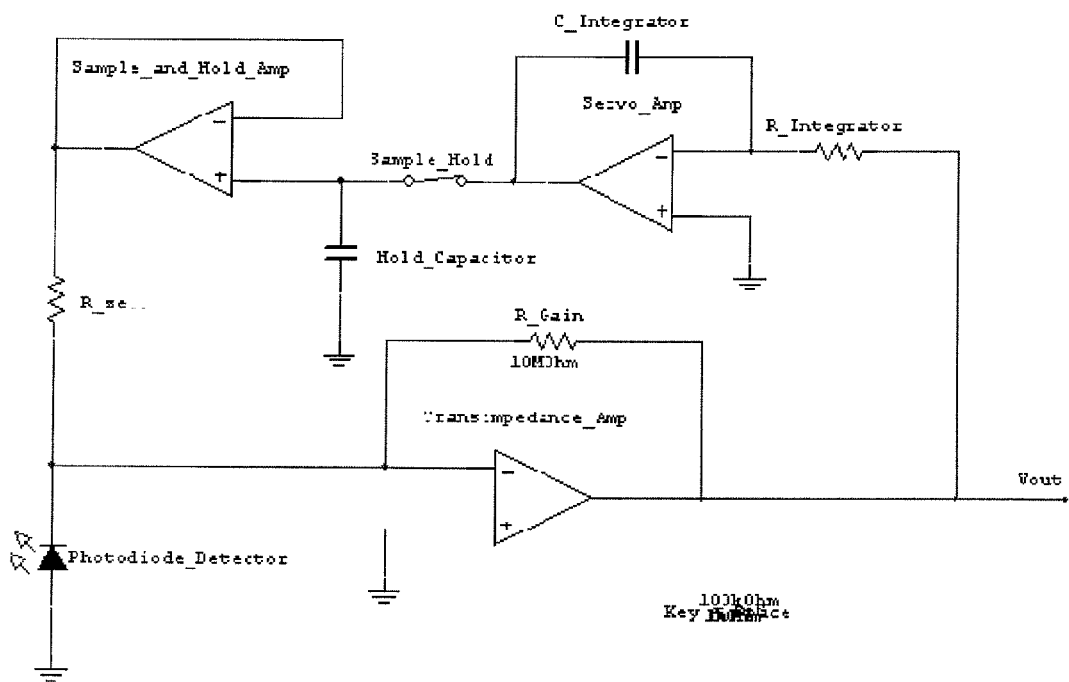
FIG. 6 is a schematic of a photodiode detector circuit according to the present invention.

An ultra-sensitive detector circuit is critical to a practical chemical sensor based on BR. Because photodiodes are current output devices, standard capacitive coupling will not work. Therefore an active AC coupling scheme such as that published in the application bulletin by Burr-Brown must be used, see Stitt, M. and W. Meinel, *OPT201 photodiode-amplifier rejects ambient light*, in *Burr-Brown Application Bulletin, AB*-061, 1993, hereby incorporated by reference. The present invention adds a sample-and-hold amplifier to increase the measurement time to accommodate long lifetime mutant samples. By using the AC coupled detector, changes in the probe beam intensity striking the photodiode smaller than one part in ten thousand can be measured. The basic circuit used is shown in FIG. 6. In particular, FIG. 6 depicts a block diagram of photodiode detector circuit where the servo amp has been drawn as an inverting amp in the diagram for clarity, however, in practice this is likely a non-inverting integrator. In the present invention, the output is followed by a second stage variable gain amplifier to allow for a greater dynamic range in the response of various mutated strains of the BR protein.

The AC coupling feature of the amplifier may be considered an "auto-zero" mechanism. When the sample and hold amplifier is set to sample, the output is forced to zero volts, and then when the amplifier is switched to hold mode, changes in the light intensity striking the photodiode can pass though as amplified changes in the output voltage. A step-by-step instruction of now the amplifier is used in practice is given below.

First, the sample and hold is set to sample. The photodiode absorbs light from the probe beam and converts the light to current. The current from the photodiode goes to a high gain amplifier. The amplifier feeds an integrator, which increases its output. The integrator output voltage is converted to current. The current is sent to the diode and supplies the current needed to balance out the steady state current. The high gain amplifier is no longer amplifying the steady state signal, and the output is zero.

Next, the sample and hold is set to hold. The photo-cycle is initiated by a pulse from the pump laser. The probe beam undergoes a small time dependent change in intensity. This change is amplified by the high gain amplifier. The amplified signal is measured by the micro-controller at specified time intervals. When the BR has gone back to the ground state, the sample and hold is set to sample, and the system goes back to 1.

A PC to control operations and process the data. The PC communicates to a micro-controller via an RS-232 serial port. The micro-controller controls the operation of the apparatus. Controls are provided for the pump beam, the probe beam, the photo-detector, and temperature of the sample. The microcontroller collects data, including the steady state probe beam intensity, the time varying probe beam intensity, and the temperature. These are sent to the PC via the serial port.

For a pump beam, the present invention is set up to use several possible sources. These include Lasiris lasers, both the diode lasers (635 nM and 685 nm) and a Lasiris Diode Pumped Solid State Laser (532 nm). These laser modules are inexpensive and highly reliable. The intensity of the lasers varies from 10 to 20 mW depending on the module. High power LEDs may also be used for pumping. The LEDs tested are similar to those currently being used in traffic lights. The pulse beam time length can be varied from 0.1 milliseconds to 20 milliseconds. Typically a pulse length of 1.0 millisecond is used.

The probe beam is derived from a standard high-intensity LED. These LEDs come in a variety of wavelengths ranging from 690 m to 430 nm. These LEDs provide a very steady light source and are powered by a constant voltage source with a resistor in series to maintain a constant current through the LED.

Figure 7:
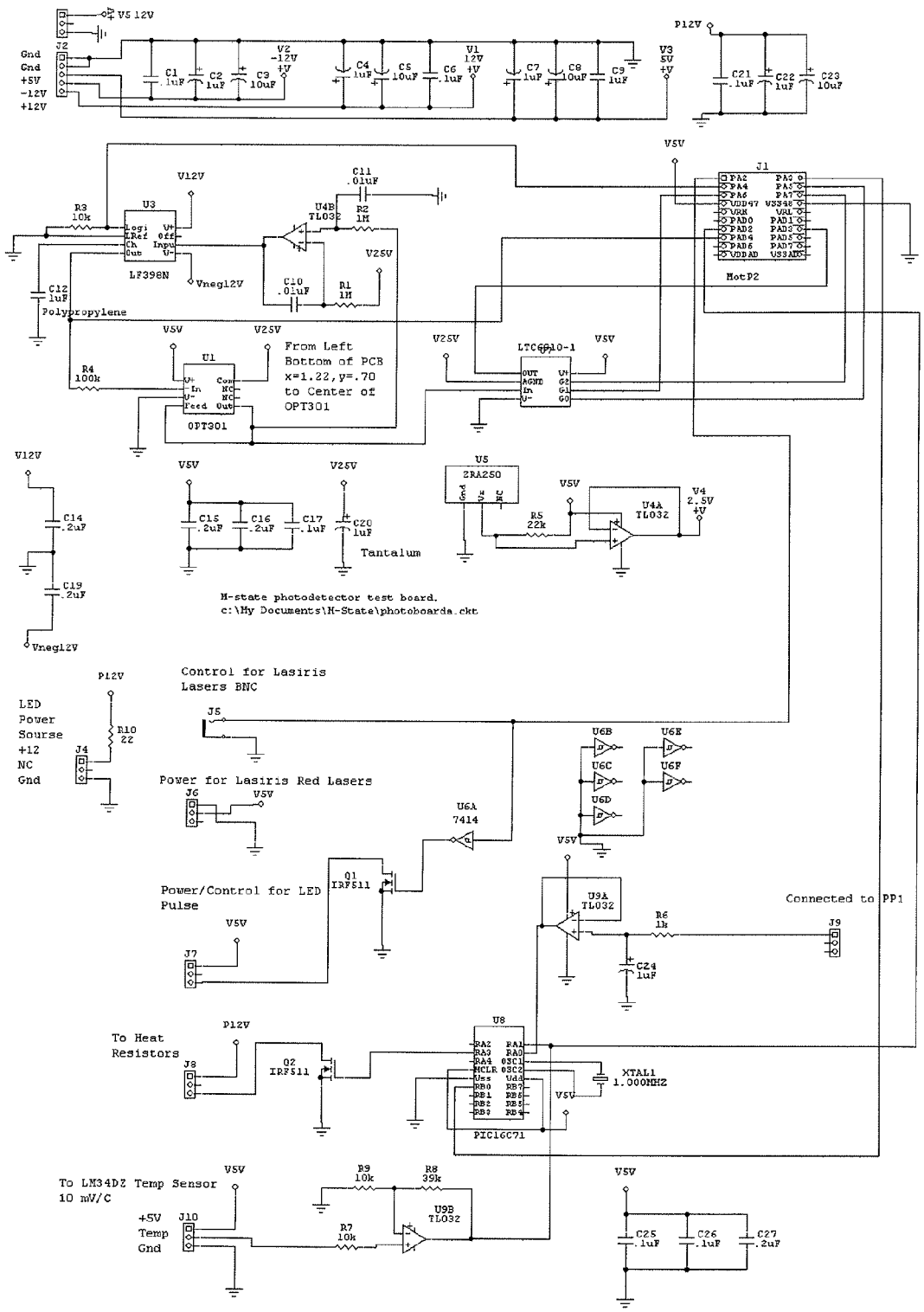
FIG. 7 is a schematic of the control electronics for a photo-detection system according to the present invention.

The photo-detector used is an OPT 101. This detector has a built in amplifier with a current to voltage gain of one million. The bandwidth is 10 kHz, allowing resolution of time dependent changes in intensity to 0.1 milliseconds. The detector is followed by a programmable gain amplifier. The gain varies from 1 to 100. Two PCBs (Printed Circuit Boards) are used for the electronics. The first has the microcontroller used to communicate with the PC. The second has the control interface electronics and the photo-detection system. The schematic for the second board is shown in FIG. 7.

Figure 8:
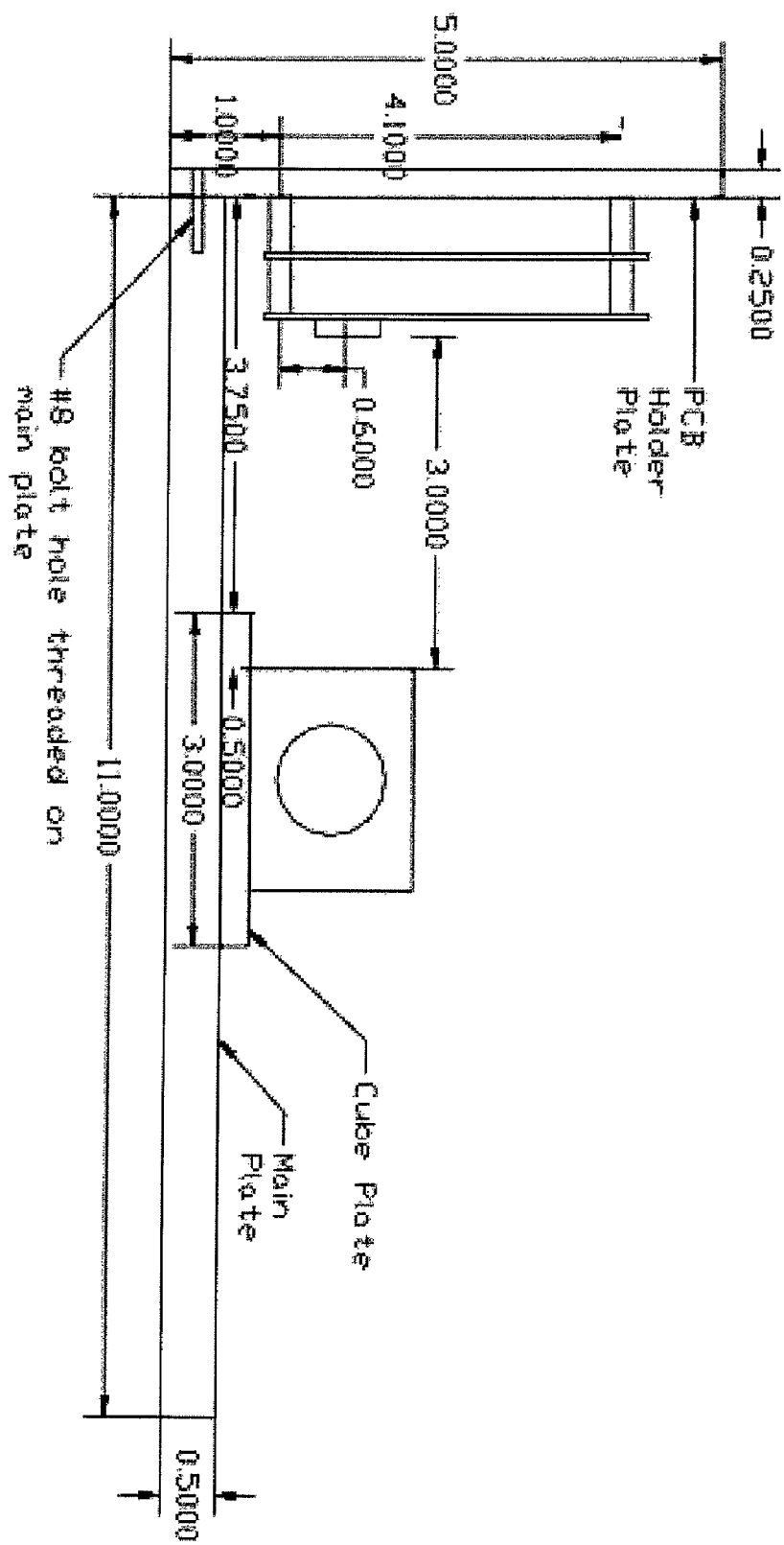
FIG. 8 is a schematic of the mechanical design of a sample detector according to the present invention.

The mechanical design for the apparatus is shown in FIG. 8, where measurements are in inches. As the primary concern is to provide a stable, vibration free system the platform is contains attachment points to make is easy to use the apparatus on an optical bench. The sample is held is a standard spectroscopy cuvette (fluorescence), thereby making it easy to prepare samples that are standardized. Other preparations of the protein, such as dried films with or without various matrices to stabilize the protein, polymers, hydrogels, sol-gels, hybrid materials, or other materials that fix the protein in place in a form that enables interrogation of the photocycle are also useful.

Figure 9:
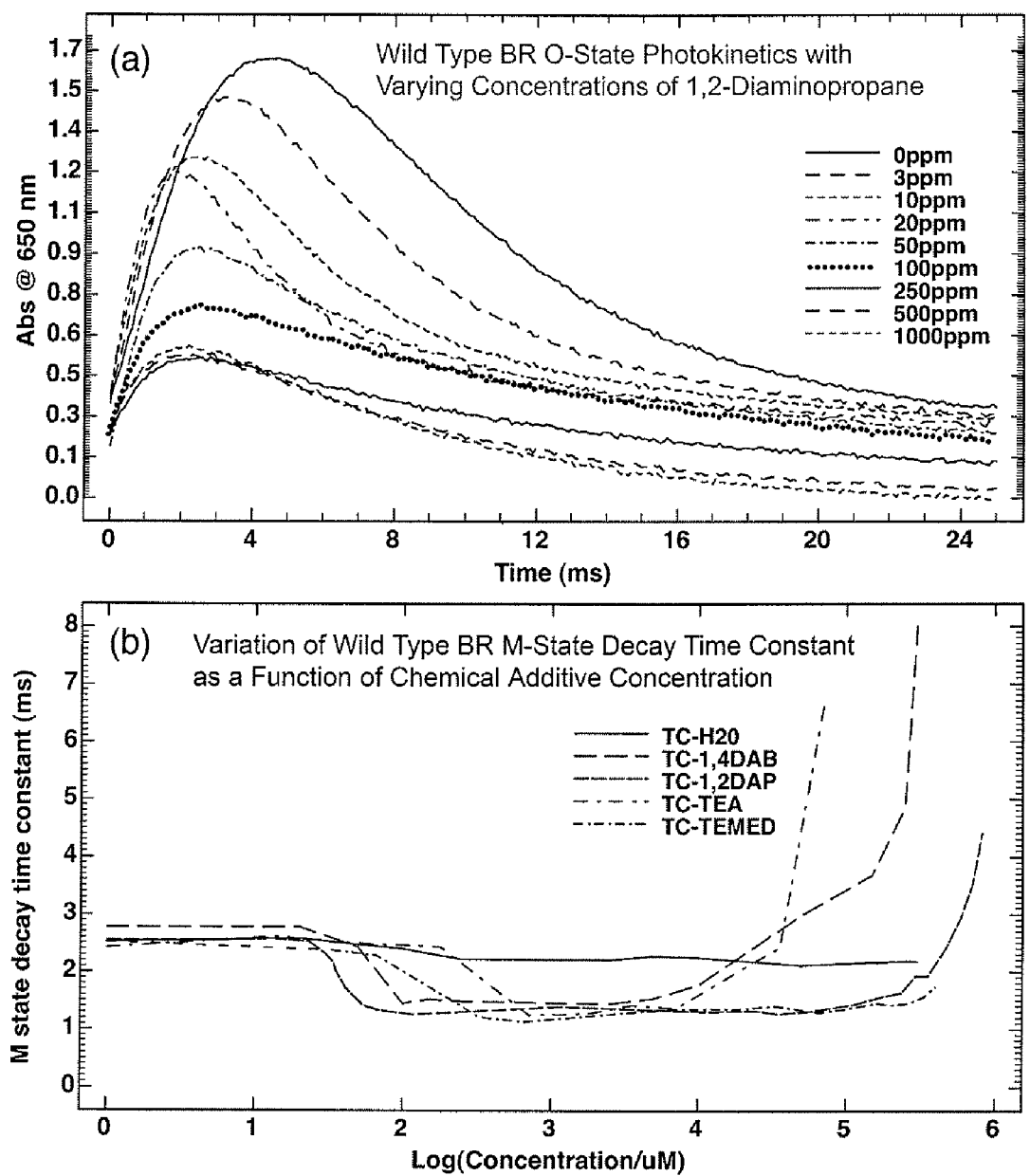
FIG. 9(a) is a graph of sample data sets showing O-state modulation as a function of the concentration of 1,2-diaminopropane.
FIG. 9(b) is a graph of sample data sets showing modulation of the M-state decay constant as a function of a selection of amine compounds.

Using the present invention, the response of the wild type protein and several mutants to a number of target chemicals was evaluated. Several amines were selected for evaluation of protein response because this class of compounds has been previously shown to affect BR photokinetics in a reproducible manner. Protein response was gauged in the presence of the target chemical in concentrations ranging from 0 ppm to 1000 ppm. Both the M- and O-states were monitored with respect to their rise and decay at select wavelengths (470 nm and 650 nm). A typical data set for O-state photokinetics is shown in FIG. 9a. Decay constants were plotted as a function of amine concentration, as illustrated for the M-state in FIG. 9b. In addition to wild-type BR, similar experiments were performed for a number of BR mutants (E204Q, T205A, and T205A/N202S), all of which behaved differently in the presence of the same selection of amines. To facilitate comparison of BR variants examined over the wide range of chemical concentrations, sensitivity was defined as the following ratio:

$$\frac{\% \text{ change in time constant or } \% \text{ change in peak height}}{\% \text{ change in chemical concentration}}$$

Figure 10:
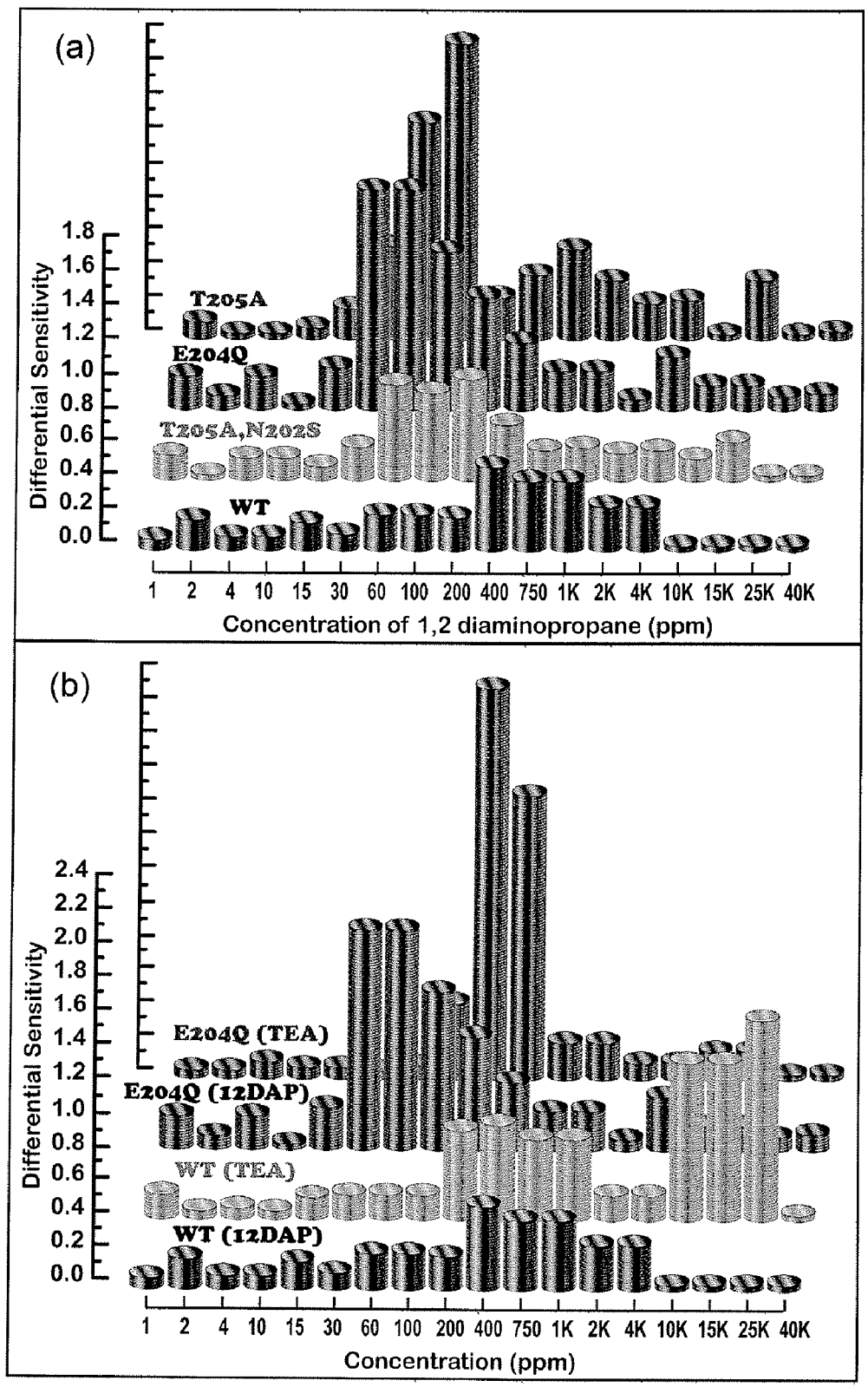
FIG. 10(a) is a chart of differential sensitivity of BR variants to a single chemical.
FIG. 10(b) is a chart of differential sensitivity of a pair of BR variants to two different chemicals.

This definition results in a unitless, quantitative method for relating the change in output to the change in input, as well as a method to compare different proteins across a large chemical range. Furthermore, a significant increase in the sensitivity range could be realized by considering only the largest parameter for each target chemical (i.e., O-state time constant, O-state peak height, and M-state time constant). Sensitivity was shown to differ between different mutants and WT to the same chemical. However, in order show that it is possible to differentiate between different chemicals it was also necessary to demonstrate different sensitivities to different chemicals. This was demonstrated by compiling the responses for a single protein to multiple chemicals, as well as the responses for multiple proteins (mutants) to a single chemical, as seen in FIG. 10.

The present invention may be used to test BR mutants for usefulness in screening a wide variety of chemicals, such as model compounds for chemical warfare agents, as well as a selection of health and environmental toxins. The latter categories include toxic industrial chemicals as identified by the NATO International Task Force 25, which, although not chemical warfare agents, could potentially be utilized as weapons in an area of engagement. Examples include, among others, boron trichloride, phosgene, ammonia, hydrogen cyanide, and a variety of acids. Many of these chemicals can be easily secured without special permit.

The BR photoelectric effect as a gauge of the protein's sensitivity to the presence of chemicals may also be evaluated using the present invention. Data analysis techniques often utilized in the characterization of chemical sensor architectures and electronic noses will be performed to facilitate comparison to other popular sensor technologies currently reported in the literature. Such statistical techniques employ multivariant analytical approaches to data sets with multiple response components (i.e., a number of different measurements extracted from one sensor reading), including a number of pattern recognition algorithms (e.g., principle component analysis and neural network approaches).

What is claimed is:

1. A sensor for detecting a target substance, comprising:
    a sensor element comprising bacteriorhodopsin;
    a probe light source for producing a probe beam directed at said sensor element;
    a pump light source for producing a pump beam directed at said sensor element; and
    a detector positioned to receive said probe beam produced by said probe light after said probe beam passes through said sensor element, wherein said detector is programmed to determine the intensity of said probe beam and the optical state of the bacteriorhodopsin when said bacteriorhodopsin is in contact with said target substance.

2. The sensor of claim 1, further comprising a lens for directing light from said probe light source onto said sensor element.

3. The sensor of claim 2, further comprising a second lens for directing light passing through said sensor element to said detector.

4. The sensor of claim 3, wherein said sensor element further comprises a housing containing said bacteriorhodopsin.

5. The sensor of claim 4, wherein said housing additionally contains said target substance.

6. The sensor of claim 1, wherein said probe light source is a monochromatic light source.

7. The sensor of claim 1, wherein said detector is programmed to determine the time-dependent change in both the intensity of said probe beam and the optical state of the bacteriorhodopsin when said bacteriorhodopsin is in contact with said target substance.

* * * * *